(12) United States Patent
Zhao et al.

(10) Patent No.: US 8,481,577 B2
(45) Date of Patent: Jul. 9, 2013

(54) AMIDE THIAZOLE DERIVATIVE, PREPARATION METHOD AND USES THEREOF

(75) Inventors: Guilong Zhao, Tianjin (CN); Weiren Xu, Tianjin (CN); Yuli Wang, Tianjin (CN); Lida Tang, Tianjin (CN); Yiliang Li, Tianjin (CN); Meixiang Zou, Tianjin (CN); Wei Liu, Tianjin (CN); Hua Shao, Tianjin (CN); Chubing Tan, Tianjin (CN); Peng Liu, Tianjin (CN)

(73) Assignee: Tianjin Institute of Pharmaceutical Research, Tianjin (CN)

( * ) Notice: Subject to any disclaimer, the term of this patent is extended or adjusted under 35 U.S.C. 154(b) by 0 days.

(21) Appl. No.: 13/162,121

(22) Filed: Jun. 16, 2011

(65) Prior Publication Data

US 2011/0281922 A1 Nov. 17, 2011

Related U.S. Application Data

(63) Continuation of application No. PCT/CN2009/001351, filed on Nov. 30, 2009.

(30) Foreign Application Priority Data

Dec. 16, 2008 (CN) .......................... 2008 1 0154154

(51) Int. Cl.
*A61K 31/427* (2006.01)
*C07D 277/46* (2006.01)

(52) U.S. Cl.
USPC .......................................... 514/371; 548/195

(58) Field of Classification Search
USPC .................... 548/196, 195; 514/371
See application file for complete search history.

(56) References Cited

U.S. PATENT DOCUMENTS 4,217,355 A * 8/1980 Harbert et al. ................ 514/371
4,305,949 A 12/1981 Harbert et al.

FOREIGN PATENT DOCUMENTS

| CN | 1633420 A | 6/2005 |
| CN | 101492427 A | 7/2009 |
| CN | 101550112 A | 10/2009 |
| WO | WO2006/128659 A2 | 12/2006 |

OTHER PUBLICATIONS

International Search Report for PCT/CN2009/001351, Mailed Mar. 18, 2010.

* cited by examiner

*Primary Examiner* — Jason M Nolan
(74) *Attorney, Agent, or Firm* — Staas & Halsey LLP

(57) ABSTRACT

The present invention relates to the field of drugs associated with treating diabetes. Particularly, the present invention relates to a dipeptidyl peptidase-IV inhibitor having the structure shown by formula (I), which contains amide thiazole structure and has an effect on treating diabetes, and a preparation method and a pharmaceutical composition containing it, as well as use thereof in manufacture of the drugs for treating the diabetes.

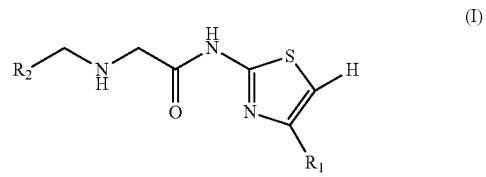

wherein, $R_1$ is methyl; $R_2$ is phenyl; phenyl, 2-thienyl substituted in a mono-substituted, bi-substituted manner by fluorine and methyl.

15 Claims, No Drawings

AMIDE THIAZOLE DERIVATIVE, PREPARATION METHOD AND USES THEREOF

CROSS REFERENCE TO RELATED APPLICATION

This application is a continuation application filed under 35 U.S.C. §111(a), claiming the benefit under 35 U.S.C. §120 and §365(c) of a PCT International Application Number PCT/CN2009/001351, filed Nov. 30, 2009, it being further noted that foreign priority benefit is based on Chinese Patent Application 200810154154.0, filed Dec. 16, 2008 in the State Intellectual Property Office of P.R. China, the disclosures of which are thereby incorporated by reference.

TECHNICAL FIELD

The present invention relates to the field of drugs associated with the diabetes. Particularly, the present invention relates to a dipeptidyl peptidase-IV inhibitor containing an amide thiazole structure and with a therapeutic effect on diabetes, and a preparation method and a pharmaceutical composition thereof, as well as use thereof in manufacture of the drugs for treating the diabetes. The present invention also relates to a method for treating the diabetes.

BACKGROUND ART

According to statistics, by far, there are approximately 0.17 billion patients suffered from diabetes over the world, about 90% of which are the patients suffered from type II (i.e. non-insulin-dependent) diabetes. Currently, the diabetes drugs used in clinical application are primarily the drugs of metformins, sulfonylureas and insulins. In recent years, the antidiabetic drugs on the market are also thiazolidinediones and α-glucosidase inhibitors and the like. These drugs possess good therapeutic effects, but lead to safety issues when being administered in long-term, e.g. liver toxicity and weight increase and the like.

Dipeptidyl peptidase IV, DPP-IV is able to degrade glucagon-like peptide-1 (GLP-1) effectively and rapidly, GLP-1 is one of the most effective stimulants in the production and secretion of insulin. Therefore, inhibitor DPP-IV is able to enhance the effect of the endogenous GLP-1, and thereby increase the insulin levels in the blood (See CN200480017355.6). Recently, medical research has already confirmed that DPP-IV inhibitor is a novel antidiabetic drug (Deacon C. F., Hoist J. J., Dipeptidyl Peptidase IV Inhibitors: A Promising New Therapeutic Approach for the Management of Type 2 Diabetes. *The International Journal of Biochemistry & Cell Biology*, 2006, 38 (5-6): 831-844). The clinical results showed that such drugs had good effect of reducing sugar without typical adverse reactions such as weight increase and hypoglycemia caused by other diabetes drugs.

SUMMARY OF THE INVENTION

Unless otherwise indicated, the terms used herein have the following definitions:

The term "pharmaceutically acceptable carriers and excipients" used herein refers to the substances well-known in the art, which are used as fillers or carriers and etc. in various dosage forms such as pellets, tablets, capsules and the like. These substances typically are recognized to apply for the specific purpose by a person skilled in the pharmaceutical industry and used as inactive ingredients of the drugs.

The term "therapeutically effective amount" used herein refers to the drug amount that produces the effective action as required, which can be changed and finally decided by medical staff. The considered factors for determining "therapeutically effective amount" include the administration routes and the formulation properties, the weights, ages and general conditions of the patients as well as the nature and severity of the disease.

Faced to the drawbacks of the safety issues of the present drug for treating the diabetes and in order to overcome the drawbacks and shortcomings in the prior art, one objective of the present invention is to provide a compound having formula (I) or a pharmaceutically acceptable salt thereof. The compound or the pharmaceutically acceptable salt thereof is a novel amide thiazole DPP-IV inhibitor, which has good activity and is able to decrease the glucose level in the blood plasma with great effectiveness, and thus providing a basis especially for the non-insulin-dependent diabetes drug for further treating diabetes.

Another objective of the present invention is to provide a method for preparing the compound having formula (I) or the pharmaceutically acceptable salt thereof.

Yet another objective of the present invention is to provide a pharmaceutical composition comprising the compound having formula (I) or the pharmaceutically acceptable salt thereof.

Still another objective of the present invention is to provide the use of the compound having formula (I) or the pharmaceutically acceptable salt thereof in manufacture of the drugs for treating the diabetes and a method for treating the diabetes by using the compound having formula (I) or the pharmaceutically acceptable salt thereof.

The objectives of the present invention described above are achieved by using the following technical solutions:

A compound having formula (I) or a pharmaceutically acceptable salt thereof, wherein,

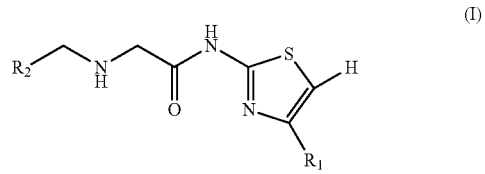

$R_1$ is methyl; and $R_2$ is phenyl; phenyl substituted in a mono-substituted, bi-substituted manner by fluorine and methyl; or 2-thienyl.

The pharmaceutically acceptable salts described above are inorganic acid salts, preferably are hydrochloride salts, sulfates, nitrates or phosphates; organic acid salts, preferably are formates, acetates, citrates, oxalates, fumarates, maleates or amino acid salts.

The examples of the compound of formula (I) or a pharmaceutically acceptable salt thereof are shown in Table 1 below:

| Code | Name of Compound |
|---|---|
| I-1 | 2-{2-[(benzyl)amino]acetyl}amino thiazole; |
| I-2 | 4-bromo-2-{2-[(2-chlorobenzyl)amino]acetyl}amino thiazole |
| I-3 | 2-{2-[(2-fluoro-4-methylbenzyl)amino]acetyl}amino-4-methyl thiazole |
| I-4 | 2-{2-[(2-cyano-3-nitryl-4-tert-butylbenzyl)amino]acetyl}amino-4-phenyl thiazole |
| I-5 | 2-{2-[(benzyl)amino]acetyl}-aminothiazole-4-methyl formate |
| I-6 | 4-methyl-2-{2-[(thienyl-2-methyl)amino]acetyl}amino thiazole |
| I-7 | 4-bromo-2-{2-[(3-bromothienyl-2-methyl)amino]acetyl}amino thiazole |
| I-8 | 2-{2-[(3-bromo-4-methylthienyl-2-methyl)amino]acetyl}amino thiazole-4-methyl formate |

| Code | Name of Compound |
|---|---|
| I-9 | 2-{2-[(furanyl-2-methyl)amino]acetyl}amino thiazole |
| I-10 | 4-bromo-2-{2-[(3-nitrylfuranyl-2-methyl)amino]acetyl}amino thiazole |
| I-11 | 2-{2-[(3-chloro-5-cyano-4-methylfuranyl-2-methyl)amino]acetyl}amino-4-methyl thiazole |
| I-12 | 2-{2-[(benzyl)amino]acetyl}amino thiazole hydrochloride |
| I-13 | 4-bromo-2-{2-[(2-chlorobenzyl)amino]acetyl}amino thiazole hydrochloride |
| I-14 | 4-methyl-2-{2-[(thienyl-2-methyl)amino]acetyl}amino thiazole hydrochloride |
| I-15 | 4-bromo-2-{2-[(3-nitrylfuranyl-2-methyl)amino]acetyl}amino thiazole hydrochloride |

A method for preparing said compound or a pharmaceutically acceptable salt thereof provided by the present invention, comprises the following steps of:

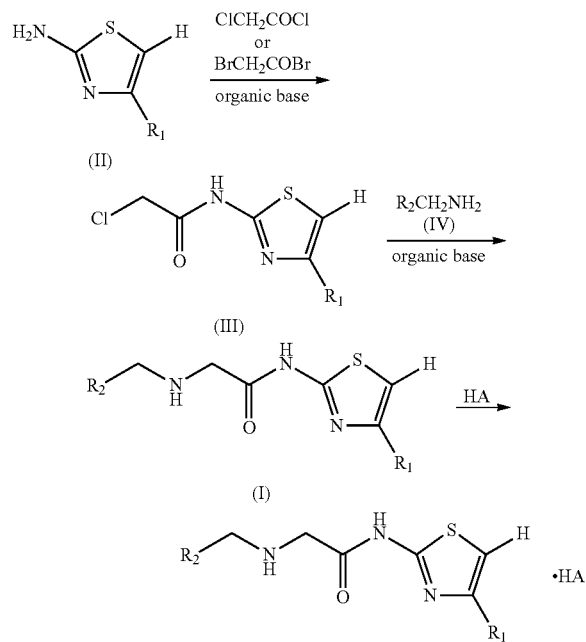

1) reacting the compound of formula (II) with chloroacetyl chloride or bromoacetyl bromide in the presence of an organic base to obtain the compound of formula (III);
2) reacting the compound of formula (III) with the compound of formula (IV) in the presence of an organic base to obtain the compound of formula (I);
3) optionally, reacting the compound of (I) with an organic acid or inorganic acid (HA) to obtain a pharmaceutically acceptable salt of said compound;
wherein, $R_1$ and $R_2$ are defined as above.

The compound of formula (II) described above can be synthesized according to the conventional Hansch's synthesis method, or can be commercial available.

In the method described above, the organic base can be one or more selected from the group consisting of triethylamine, diisopropylethylamine, pyridine, 2,6-dimethylpyridine and 4-dimethylaminepyridine.

A pharmaceutical composition provided by the present invention comprises therapeutically effective amount of the compound or the pharmaceutically acceptable salt thereof described above. The pharmaceutical composition can further comprise one or more pharmaceutically acceptable carriers, excipients and/or diluents. The compound composition can further comprise one or more pharmaceutically acceptable adjuvants selected from the group consisting of fillers, adhesives, disintegrants, lubricants, flow aids, effervescing agents, flavoring agents, preservatives and coating materials and the like. Wherein, the fillers comprise one or more of lactose, sucrose, dextrin, starch, pregelatinized starch, mannitol, sorbitol, dibasic calcium phosphate, calcium sulfate, calcium carbonate or microcrystalline cellulose; the adhesives comprise one or more of sucrose, starch, polyvidon, carboxymethylcellulose sodium, hydroxypropylmethyl cellulose, hydroxypropyl cellulose, methyl cellulose, polyglycol, ethanol for medical use or water; the disintegrants comprise one or more of starch, crosslinked polyvidon, crosslinked carboxymethyl cellulose sodium, low substituted hydroxypropyl cellulose, carboxymethyl cellulose sodium or effervescent disintegrant.

The pharmaceutical composition described above can be solid oral formulations, liquid oral formulations or injections. In particular, the solid or liquid oral formulations can be tablets, dispersible tablets, enteric-coated tablets, chewing tablets, orally disintegrating tablets, capsules, granules or oral solutions; the injections can be liquid injections, lyophilized powder injections, large infusions or small infusions.

The present invention provides the use of the above mentioned compound having formula (I) or the pharmaceutically acceptable salt thereof in manufacture of the drugs for treating the diabetes; preferably, the diabetes is non-insulin-dependent diabetes.

The present invention provides a method for treating diabetes, which comprises administering therapeutically effective amount of the compound or the pharmaceutically acceptable salt thereof to the patients. The compound of formula (I) or the pharmaceutically acceptable salt thereof of the present invention is effective in a broad range of dosage, and preferably, the therapeutic amount of the compound or the pharmaceutically acceptable salt thereof is in range of 1 mg~1000 mg/person/day. The compound or the pharmaceutically acceptable salt thereof described above can be administered at one time or at several times. The actual administered dosage of the compound or the pharmaceutically acceptable salt thereof of the present invention can be determined by the doctors according to the related conditions. Such conditions include the physical status of the subjects, the administration routes, ages, weights, personal reaction to the drugs, the severity of the symptoms and the like.

The compound of formula (I) or the pharmaceutically acceptable salt thereof of the present invention has the inhibitory effect of DPP-IV, which thus can be used as effective ingredients for preparing the drugs for treating diabetes; preferably, the type of diabetes is non-insulin-dependent diabetes. The activity of the compound or the pharmaceutically acceptable salt thereof of the present invention can be testified by the sugar-reducing model in vivo. The test shows that the compound or the pharmaceutically acceptable salt thereof of the present invention is a novel amide thiazole DPP-IV inhibitor, which is able to decrease the glucose level in the blood plasma with great effectiveness, and thus providing a basis especially for the non-insulin-dependent diabetes drug for further treating the diabetes.

PREFERRED EMBODIMENTS OF THE INVENTION

The present invention will be further illustrated with reference to the following examples. It is necessary to state that, the examples below are only for illustration, but not for limitation. Various alterations that are made by a person skilled in the art in accordance with the teachings from the present invention should be within the protection scope claimed by the claims of the present invention.

Example 1

Preparation of 2-(2-chloroacetyl)amino-4-methylthiazole (III-1)

1.14 g of compound II-1 (10 mmol), 1.31 g of dry triethylamine (13 mmol) and 50 mL of dry $CH_2Cl_2$ are added into a 100 mL of round-bottom flask to form a mixture. The mixture is cooled with an ice-water bath under stirring. Then 1.24 g of the solution of chloroacetyl chloride (11 mmol) dissolved in 5 mL of dry $CH_2Cl_2$ is added dropwise slowly, after completion, the reaction mixture is stirred for 1 hour under the room temperature. The reaction mixture is diluted with 50 mL of $CH_2Cl_2$, followed by washed with the saturated saline. The organic phase is dried by anhydrous $Na_2SO_4$, and then the solvent is removed on the rotary evaporator. The resulting residue is purified by column chromatography to obtain the pure product of compound III-1, 1.75 g, and the yield is 92%. The product is a colorless crystal, and the melting point is 128-129° C., and the peak values of IR (KBr) are 3185, 3053, 1653, 1578 and 1380 $cm^{-1}$. The compounds of II-1 and III-1 are one of the compounds having general formula II and III, respectively.

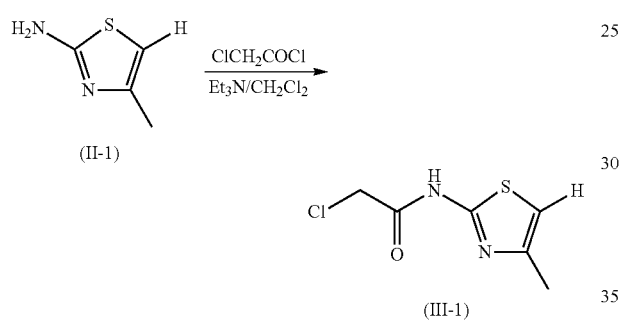

(II-1)

(III-1)

Examples 2-5

The procedure is the same with that of Example 1, except for:

the compound II-1 in Example 1 is replaced by the compounds II-2 to II-5 shown in Table 2, and triethylamine in Example 1 is replaced by other organic bases such as diisopropylethylamine or 4-dimethylaminepyridine in some of the Examples with the remaining procedures are the same with Example 1 to obtain the compounds III-2 to III-5 listed in Table 2.

The compounds II-2 to II-5 and compounds III-2 to III-5 are the two types of compounds having general formula II and III, respectively.

The characterization data of the compounds III-2 to III-5 listed in Table 2 are as follows:

III-2: 2-(2-chloroacetyl)aminothiazole: colorless crystal, melting point, 167-169° C., IR (KBr), 3187, 3031, 1654 $cm^{-1}$.

III-3: 4-bromo-2-(2-chloroacetyl)aminothiazole: colorless crystal, IR (KBr), 3178, 3032, 1656 $cm^{-1}$.

III-4: 2-(2-chloroacetyl)amino-4-phenylthiazole: colorless crystal, melting point 144-145° C., $^1$H NMR (DMSO-$d_6$, 400 MHz), 7.82-7.85 (m, 2H), 7.42-7.46 (m, 2H), 7.34-7.37 (m, 1H), 7.20 (s, 1H), 4.22 (s, 2H).

III-5: 2-(2-chloroacetyl)aminothiazole-4-methyl formate: colorless crystal, IR (KBr), 3182, 3030, 1691, 1656 $cm^{-1}$.

Example 6

Preparation of 4-bromo-2-{2-[(2-chlorobenzyl)amino]acetyl}aminothiazole (I-1)

(III-2)

(I-1)

1.77 g of compound III-2 (10 mmol), 1.61 g of benzylamine (IV-1) (15 mmol) and 1.01 of triethylamine (10 mmol) are added into a 100 mL of round-bottom flask, and then 25 mL of dry THF is added for dissolving. The resulting reaction mixture is stirred overnight under the room temperature. The solvent in the reaction mixture is removed on the rotary evaporator to obtain the crude product of compound I-1, which is purified by column chromatography to obtain the pure product of compound I-1. The product is colorless oil, 2.22 g, and the yield is 90%. The peak values of IR (KBr) are 3237, 3186, 3030, 1654 $cm^{-1}$; and $^1$H NMR (DMSO-$d_6$, 400 MHz), δ 7.446-7.454, 7.20-7.21 (2d, 1H each, J=3.2 Hz and 3.6 Hz), 7.29-7.35 (m, 4H), 7.21-7.24 (m, 1H), 3.73 (s, 2H), 3.41 (s, 2H).

TABLE 2

Products of III-2 to III-5 obtained from Examples 2-5

| Ex. No. | Yield (%) | Organic Base | II | III |
|---|---|---|---|---|
| 2 | 92 | diisopropylethylamin | II-2: 2-aminothiazole | III-2: 2-(2-chloroacetyl)aminothiazole |
| 3 | 90 | 4-dimethylaminepyridine | II-3: 2-amino-4-bromothiazole | III-3: 4-bromo-2-(2-chloroacetyl)aminothiazole |
| 4 | 95 | diisopropylethylamin | II-4: 2-amino-4-phenylthiazole | III-4: 2-(2-chloroacetyl)amino-4-phenylthiazole |
| 5 | 91 | triethylamine | II-5: 2-aminothiazole-4-methyl formate | III-5: 2-(2-chloroacetyl)aminothiazole-4-methyl formate |

The compounds of IV-1 and I-1 are the one of the compounds having general formula IV and I, respectively.

Examples 7-16

The procedure is the same with that of Example 1, except for:

the compound III-2 (in some of the Examples, the compound of III-2 is still used) in Example 6 is replaced by the compounds III-1 to III-5 shown in Table 3, and the compound IV-1 in Example 6 (in some of the Examples, the compound of IV-1 is still used) is replaced by compounds IV-2 to IV-10. Triethylamine in Example 1 is replaced by diisopropylethylamine, pyridine, 2,6-dimethyl pyridine or 4-dimethylaminepyridine in some of the Examples with the remaining procedures are the same with that of Example 6 to obtain the compounds I-2 to I-11 listed in Table 3.

The compounds IV-2 to IV-10 and compounds I-2 to I-11 are the two types of compounds having general formula IV and I, respectively.

I-3: 2-{2-[(2-fluoro-4-methylbenyl)amino]acetyl}amino-4-methyl thiazole: colorless crystal, IR (KBr), 3240, 3185, 3032, 1652 cm$^{-1}$.

(I-4) 2-{2-[(2-cyano-3-nitryl-4-tert-butylbenyl)amino]acetyl}amino-4-phenyl thiazole, colorless crystal, IR (KBr), 3218, 3182, 3033, 2223, 1654 cm$^{-1}$.

(I-5) 2-{2-[(benyl)amino]acetyl}-aminothiazole-4-methyl formate, colorless crystal, IR (KBr), 3237, 3183, 3030, 1694, 1655 cm$^{-1}$.

(I-6) 4-methyl-2-{2-[(thienyl-2-methyl)amino]acetyl}amino thiazole, colorless crystal, $^1$H NMR (CDCl$_3$, 400 MHz), δ 7.23-7.24 (m, 1H), 6.94-6.95 (m, 2H), 6.518-6.520 (d, 1H, J=0.8 Hz), 4.04 (s, 2H), 3.52 (s, 2H), 2.350-2.352 (d, 3H, J=0.8 Hz).

(I-7) 4-bromo-2-{2-[(3-bromothienyl-2-methyl)amino]acetyl}amino thiazole: colorless crystal, IR (KBr), 3245, 3188, 3028, 1655 cm$^{-1}$.

(I-8) 2-{2-[(3-bromo-4-methylthienyl-2-methyl)amino]acetyl}amino thiazole-4-methyl formate, colorless crystal, IR (KBr), 3236, 3179, 3032, 1693, 1657 cm$^{-1}$.

TABLE 3

Products I-2 to I-11 obtained from Examples 7-16

| Ex. No. | Yield % | Organic Base | III | IV | I |
|---|---|---|---|---|---|
| 7 | 90 | triethylamine | III-3 | IV-2: 2-chlorobenzylamine | I-2: 4-bromo-2-{2-[(2-chlorobenyl)amino]acetyl}amino thiazole |
| 8 | 91 | pyridine | III-1 | IV-3: 2-fluoro-4-methyl benzylamine | I-3: 2-{2-[(2-fluoro-4-methylbenyl)amino]acetyl}amino-4-methyl thiazole |
| 9 | 90 | diisopropylethyl amine | III-4 | IV-4: 2-cyano-3-nitryl-4-tert-butylbenzylamine | I-4: 2-{2-[(2-cyano-3-nitryl-4-tert-butylbenyl)amino]acetyl}amino-4-phenyl thiazole |
| 10 | 89 | 2,6-dimethyl pyridine | III-5 | IV-1: benzylamine | I-5: 2-{2-[(benyl)amino]acetyl}-aminothiazole-4-methyl formate |
| 11 | 92 | 4-dimethyl amine pyridine | III-1 | IV-5: thienyl-2-methylamine | I-6: 4-methyl-2-{2-[(thienyl-2-methyl)amino]acetyl}amino thiazole |
| 12 | 95 | triethylamine | III-3 | IV-6: 3-bromothienyl-2-methylamine | I-7: 4-bromo-2-{2-[(3-bromothienyl-2-methyl)amino]acetyl}amino thiazole |
| 13 | 92 | diisopropylethyl amine | III-5 | IV-7: 3-bromo-4-methyl thienyl-2-methylamine | I-8: 2-{2-[(3-bromo-4-methylthienyl-2-methyl)amino]acetyl}amino thiazole-4-methyl formate |
| 14 | 90 | 4-dimethyl amine pyridine | III-2 | IV-8: furanyl-2-methylamine | I-9: 2-{2-[(furanyl-2-methyl)amino]acetyl}amino thiazole |
| 15 | 88 | pyridine | III-3 | IV-9: 3-nitryl-furanyl-2-methylamine | I-10: 4-bromo-2-{2-[(3-nitrylfuranyl-2-methyl)amino]acetyl}amino thiazole |
| 16 | 89 | 2,6-dimethyl pyridine | III-1 | IV-10: 3-chloro-5-cyano-4-methylfuranyl-2-methylamine | I-11: 2-{2-[(3-chloro-5-cyano-4-methylfuranyl-2-methyl)amino]acetyl}amino-4-methyl thiazole |

The characterization data of the compounds I-2 to I-11 listed in Table 3 are as follows:

I-2: 4-bromo-2-{2-[(2-chlorobenyl)amino]acetyl}amino thiazole: colorless crystal, IR (KBr), 3233, 3185, 3030, 1657 cm$^{-1}$.

(I-9) 2-{2-[(furanyl-2-methyl)amino]acetyl}amino thiazole, colorless crystal, melting point is 115-117° C., IR (KBr), 3233, 3189, 3030, 1652 cm$^{-1}$.

(I-10) 4-bromo-2-{2-[(3-nitrylfuranyl-2-methyl)amino]acetyl}amino thiazole, colorless crystal, IR (KBr), 3231, 3177, 3018, 1658 cm$^{-1}$.

(I-11) 2-{2-[(3-chloro-5-cyano-4-methylfuranyl-2-methyl)amino]acetyl}amino-4-methyl thiazole, colorless crystal, IR (KBr), 3241, 3189, 3030, 2227, 1654 cm$^{-1}$.

Example 17
Preparation of 2-{2-[(benzyl)amino]acetyl}aminothiazole hydrochloride (I-12)

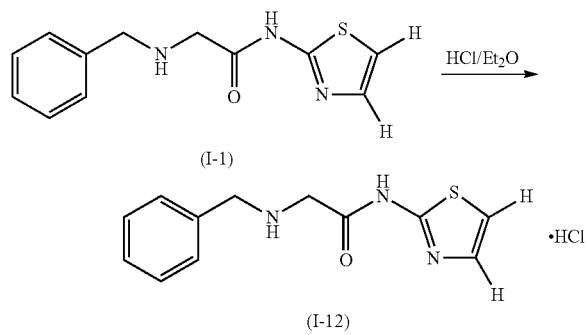

2.47 g of compound I-1 (10 mmol) is added into a 50 mL of round-bottom flask and dissolved by 20 mL of anhydrous ether, and 10% HCL-ether solution is added in dropwise with stirring under the room temperature. After completion, the mixture is stirred for half an hour under the room temperature. The precipitate is collected by filtration and dried to obtain the chloride salt I-12 of the compound I-1. The product is in the form of white powders with the weight of 2.78 g. The yield is 98%, and melting point is 202-204° C. (decomposition).

The compound of I-12 is one of the compounds having the general formula I, and is the chloride salt of the compound I-1.

Example 18-20

The procedure is the same with that of Example 17, except for:
the compound I-1 in Example 17 is replaced by the compounds of I-2, I-6 and I-10 listed in Table 4, respectively to obtain their corresponding chloride salts I-13 to I-15.

TABLE 4

Products I-13 to I-15 obtained from examples 18-20

| Ex. No. | Yield % | I | I |
|---|---|---|---|
| 18 | 99 | I-2: 4-bromo-2-{2-[(2-chlorobenyl)-amino]acety}amino thiazole | I-13: 4-bromo-2-{2-[(2-chlorobenyl)]-acetyl}amino-thiazole hydrochloride |
| 19 | 98 | I-6: 4-methyl-2-{2-[(thienyl-2-methyl)-amino]acetyl}amino thiazole | I-14: 4-methyl-2-{2-[(thienyl-2-methyl)-amino]acetyl}amino thiazole hydrochloride |
| 20 | 97 | I-10: 4-bromo-2-{2-[(3-nitrylfuranyl-2-methyl)amino]acetyl}amino thiazole | I-15: 4-bromo-2-{2-[(3-nitrylfuranyl-2-methyl)amino]-acetyl}aminothiazole hydrochloride |

The characterization data of the compounds I-13 to I-15 listed in Table 4 are as follows:

I-13: 4-bromo-2-{2-[(2-chlorobenyl)]acetyl}amino thiazole hydrochloride: white powders, melting point 198-200° C. (decomposition)

I-14: 4-methyl-2-{2-[(thienyl-2-methyl)amino]acetyl}amino thiazole hydrochloride: white powders, melting point 181-183° C. (decomposition)

I-15: 4-bromo-2-{2-[(3-nitrylfuranyl-2-methyl)amino]acetyl}amino thiazole hydrochloride, white powders, melting point 210-203° C. (decomposition)

Example 21

| | amount/capsule |
|---|---|
| sample (I-6) in Example 11 | 50 mg |
| microcrystalline cellulose | 30 mg |
| pregelatinized starch | 20 mg |
| polyvinyl pyrrolidone | 3 mg |
| magnesium stearate | 2 mg |
| talc powders | 1 mg |

The active ingredient, pregelatinized starch and microcrystalline cellulose are sieved and mixed sufficiently, and then polyvinyl pyrrolidone solution is added and mixed to make soft materials. The soft materials are sieved to make wet granules, which are dried under the temperature of 50-60° C. Magnesium stearate and talc powders are pre-sieved, and then added to said granules for capsulizing to obtain the final product.

Example 22

| | amount/50 mL |
|---|---|
| sample (I-14) in Example 19 | 50 mg |
| citric acid | 100 mg |
| NaOH | q.s. (for adjusting pH to 4.0-5.0) |
| distilled water | 50 mL |

The distilled water and citric acid are firstly added into the distilled water. After stirring to dissolved, the sample is then added, and heated slightly for dissolving. pH value is adjusted to 4.0-5.0, and 0.2 g of active carbon is added in. The mixture is stirred for 20 minutes under the room temperature and then filtered. The filtrate, the concentration of which is determined by a central-controlled manner, is batched in 5 mL ampoule and sterilized for 30 minutes at elevated temperature to obtain the injection.

Example 23

1% sodium carboxymethyl cellulose is used to formulate the sample to a suspension with the concentration of 5 mg/mL, the administration amount is 0.4 mL/20 g body weight, which is corresponding to 100 mg/kg dosage.

The health ICR mice with 20-24 g of body weight fulfill the primary standard, and the male and female of them are in equal. The animals are fasted for 16 hours, and 2 g/kg of glucose-saline solution is injected intraperitoneally at 2 h after administration (glucose is injected at 1.5 h after administration of diamicron). The blood is regularly collected from the post-glomus venous plexus in mice with capillary at 0.5 h, 1 h, 2 h, 3 h, and 4 h after modeling, centrifuged to separate the blood serum, and the content of serum glucose is measured at each of the time-point by glucose-oxidase method. The results are shown in Table 5.

TABLE 5

| | | Glucose content in serum measured by glucose-oxidase method at each time | | | | |
|---|---|---|---|---|---|---|
| groups | dose (mg/kg) | 0.5 h blood sugar (mg/dl) | 1 h blood sugar (mg/dl) | 2 h blood sugar (mg/dl) | 3 h blood sugar (mg/dl) | 4 h blood sugar (mg/dl) |
| model | | 388.2 ± 43.3 | 260.8 ± 31.2 | 147.3 ± 26.9 | 93.3 ± 21.2 | 98.2 ± 8.5 |
| diamicron | 100 | 211.0 ± 91.3 | 140.3 ± 74.4 | 103.4 ± 31.7 | 77.2 ± 25.8 | 62.3 ± 22.3 |
| I-1 | 100 | 266.4 ± 56.9 | 182.3 ± 57.6 | 88.2 ± 17.6 | 60.0 ± 15.6 | 52.3 ± 28.1 |
| I-2 | 100 | 199.2 ± 37.6 | 153.3 ± 62.7 | 93.3 ± 48.7 | 58.2 ± 29.0 | 60.0 ± 18.2 |
| I-6 | 100 | 240.1 ± 41.1 | 186.8 ± 45.9 | 113.6 ± 30.9 | 76.6 ± 48.4 | 88.0 ± 20.1 |
| I-7 | 100 | 186.0 ± 67.8 | 130.2 ± 37.7 | 100.9 ± 29.6 | 83.3 ± 91.8 | 72.1 ± 29.7 |
| I-8 | 100 | 162.5 ± 20.6 | 102.0 ± 30.5 | 98.7 ± 20.5 | 62.5 ± 15.3 | 50.6 ± 18.9 |
| I-13 | 100 | 195.6 ± 78.1 | 166.5 ± 44.2 | 99.3 ± 20.9 | 68.1 ± 21.5 | 59.2 ± 18.3 |
| I-14 | 100 | 233.2 ± 18.1 | 176.2 ± 25.2 | 95.4 ± 46.9 | 65.3 ± 20.1 | 70.1 ± 15.3 |
| I-15 | 100 | 193.6 ± 76.4 | 161.5 ± 42.6 | 91.3 ± 20.0 | 64.1 ± 20.2 | 55.1 ± 14.2 |

The results show that each administration is able to significantly reduce blood sugar tolerance of the mice induced by glucose.

What is claimed is:

1. A method for treating diabetes, comprising administering therapeutically effective amount of a compound having formula (I) or a pharmaceutically acceptable salt thereof to a patient,

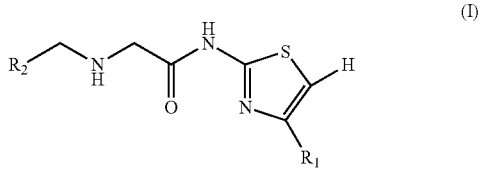

(I)

wherein, $R_1$ is methyl; and
$R_2$ is phenyl substituted in a mono-substituted or bi-substituted manner by fluorine and methyl; or 2-thienyl.

2. The method according to claim 1, wherein, the pharmaceutically acceptable salt is inorganic acid salt or organic acid salt.

3. The method according to claim 1, wherein, the compound or the pharmaceutically acceptable salt thereof is:
(I-3)    2-{2-[(2-fluoro-4-methylbenzyl)amino]acetyl}amino-4-methyl thiazole; or
(I-14)    4-methyl-2-{2-[(thienyl-2-methyl)amino]acetyl}amino thiazole hydrochloride.

4. A method for treating the diabetes, comprising administering a pharmaceutical composition to the patient, wherein the pharmaceutical composition comprises therapeutically effective amount of the compound or the pharmaceutically acceptable salt thereof according to claim 1.

5. The method according to claim 4, wherein the pharmaceutical composition further comprises one or more pharmaceutically acceptable carriers, excipients and/or diluents.

6. The method according to claim 2, wherein, the compound or the pharmaceutically acceptable salt is:
(I-3)    2-{2-[(2-fluoro-4-methylbenzyl)amino]acetyl}amino-4-methyl thiazole; or
(I-14)    4-methyl-2-{2-[(thienyl-2-methyl)amino]acetyl}amino thiazole hydrochloride.

7. A method for treating diabetes, comprising administering a pharmaceutical composition to the patient, wherein the pharmaceutical composition comprises therapeutically effective amount of the compound or the pharmaceutically acceptable salt thereof according to claim 2.

8. The method according to claim 7, wherein the pharmaceutical composition further comprises one or more pharmaceutically acceptable carriers, excipients and/or diluents.

9. A method for treating the diabetes, comprising administering a pharmaceutical composition to the patient, wherein the pharmaceutical composition comprises therapeutically effective amount of the compound or the pharmaceutically acceptable salt thereof according to claim 3.

10. The method according to claim 9, wherein the pharmaceutical composition further comprises one or more pharmaceutically acceptable carriers, excipients and/or diluents.

11. A method for treating the diabetes, comprising administering therapeutically effective amount of the compound or the pharmaceutically acceptable salt thereof according to claim 2 to the patients, preferably, the therapeutic amount of the compound or the pharmaceutically acceptable salt thereof is in range of 1 mg~1000 mg/person/day.

12. A method for treating the diabetes, comprising administering therapeutically effective amount of the compound or the pharmaceutically acceptable salt thereof according to claim 3 to the patients, preferably, the therapeutic amount of the compound or the pharmaceutically acceptable salt thereof is in range of 1 mg~1000 mg/person/day.

13. The method according to claim 2, wherein the inorganic acid salt is hydrochloride salt, sulfate, nitrate or phosphate.

14. The method according to claim 2, wherein the organic acid salt is formate, acetate, citrate, oxalate, fumarate, maleate or amino acid salt.

15. The method claimed in claim 1, wherein the therapeutic amount of the compound or the pharmaceutically acceptable salt thereof is in range of 1 mg~1000 mg/person/day.

* * * * *